US00PP12600P2

(12) United States Plant Patent
Noodelijk

(10) Patent No.: US PP12,600 P2
(45) Date of Patent: Apr. 30, 2002

(54) CHRYSANTHEMUM PLANT NAMED 'CARTER'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/561,911

(22) Filed: May 1, 2000

(51) Int. Cl.[7] ..... A01H 5/00
(52) U.S. Cl. ..... Plt./292
(58) Field of Search ..... Plt./292

*Primary Examiner*—Bruce R. Campbell
*Assistant Examiner*—A Para
(74) *Attorney, Agent, or Firm*—Parkhurst & Wendel, L.L.P.

(57) ABSTRACT

A Chrysanthemum plant named 'CARTER' characterized by its large sized blooms with pink ray-florets and no disc florets.

2 Drawing Sheets

BACKGROUND OF THE INVENTION

'CARTER' is a product of a breeding-program which had the objective of creating new chrysanthemum cultivars with a decorative type flower, a 7 week response and a medium plant height. The new plant of the present invention comprises a new and distinct cultivar of Chrysanthemum plant 'CARTER' is a seedling from a cross in a breeding program maintained under the control of inventor. The female parent is #93.601-unpatented-, an unnamed seedling not available to inventor for description. The male parent is unknown, being a mixed pollation of a group of male parents. The new and distinct cultivar was discovered and selected as a flowering plant within the progeny of the stated cross by Rob Noodelijk in a controlled environment (greenhouse) in Rijsenhout Holland in May 1998.The first act of asexual reproduction of 'CARTER' was accomplished when vegetative cuttings were taken from the initial selection in August 1998 in a controlled environment in Rijsenhout Holland.

SUMMARY OF THE INVENTION

The present invention is a new and distinct variety of chrysanthemum bearing large sized double blooms with pink ray-florets and no disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
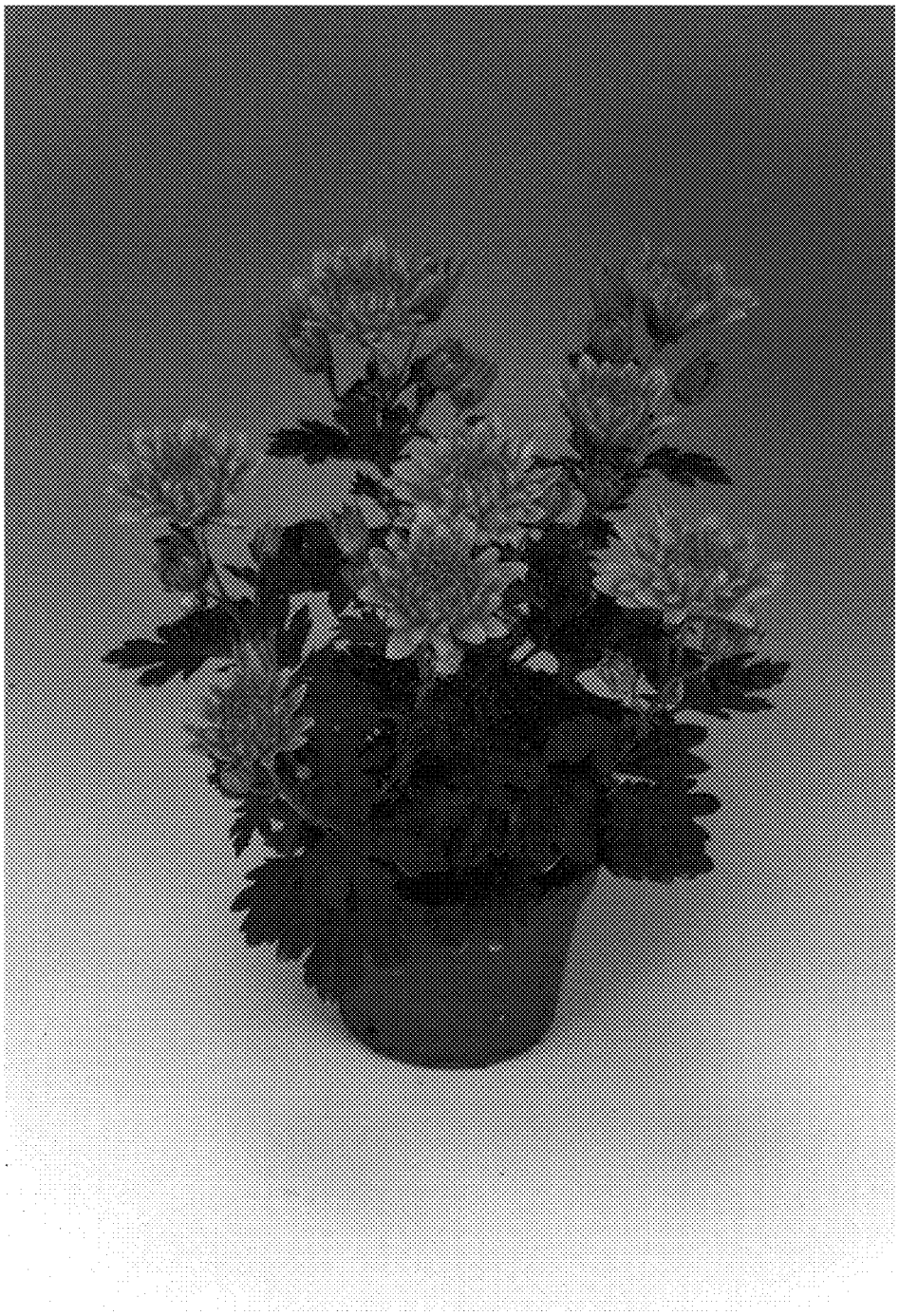
FIG. 1 shows a plant of the cultivar in full bloom.
Figure 2:
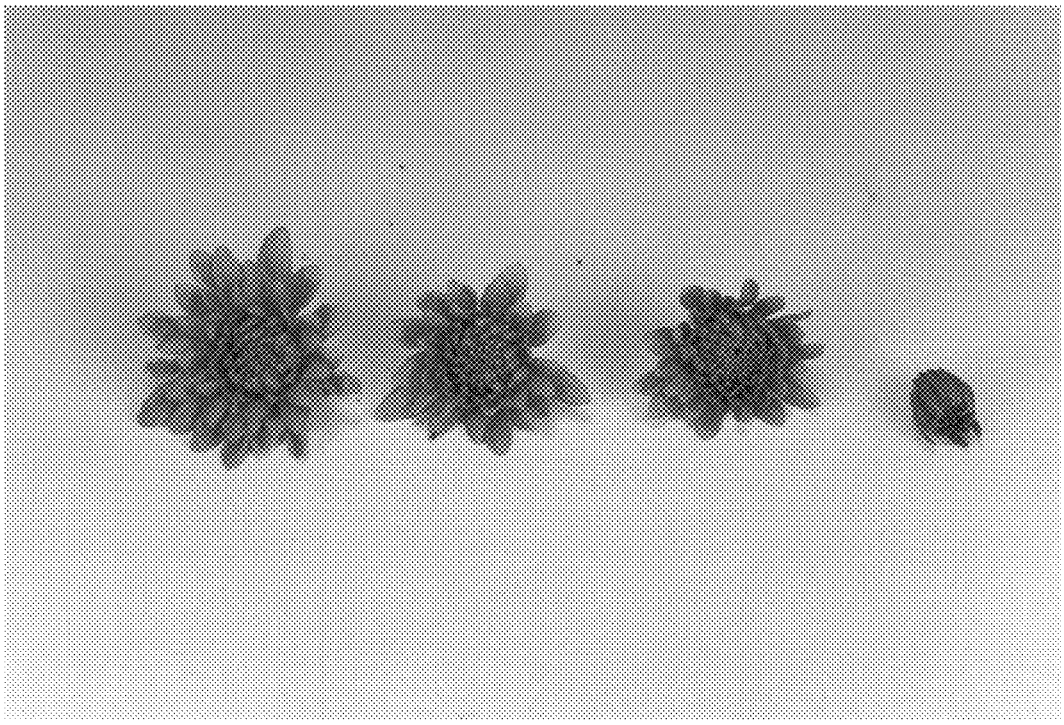
FIG. 2 shows the various stages of bloom of the new cultivar.
Figure 3:
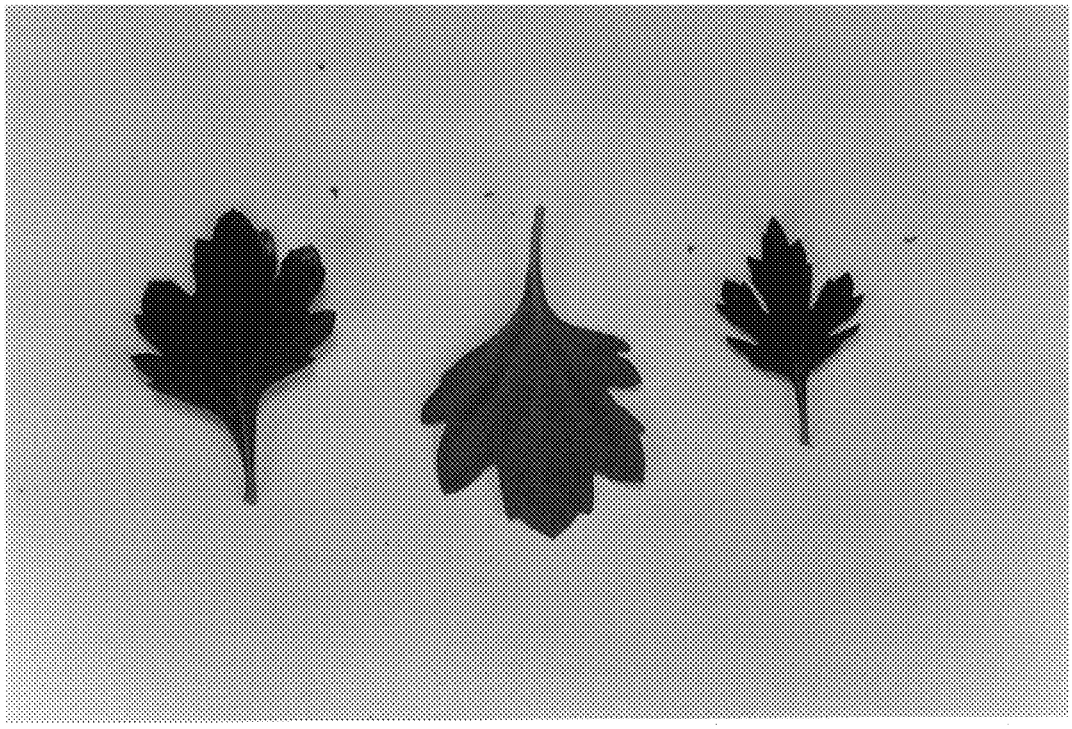
FIG. 3. shows the various stages of foliage and petiole of the new cultivar.

This new variety of chrysanthemum is of the botanical classification *Dendranthema grandiflora*. The observations and measurements were gathered from 63-day plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 55 days after an average of eight long days. After this long day period to flowering growth retardants were applied 6 times in an average dose of 1.5 gram/liter water. The plants were observed (directly) during the flowering of this crop. No tests were done on disease or insect resistance of susceptibility. No tests were done on cold or drought tolerance. This new variety produces large sized blooms with pink ray-florets and no disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'CARTER' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known in inventor the most similar existing cultivar in comparison to 'CARTER' is 'DARK CHARM' (p.p. 7585). When 'DARK CHARM' (p.p. 7585) and 'CARTER' are being compared the following differences are noticed: The differences of 'DARK CHARM' (p.p. 7585) and 'CARTER' are the flower shape. The ray-florets of 'CARTER' are less reflexing than the ray-florets of 'DARK CHARM' (p.p. 7585). The ray-florets of 'CARTER' are not so pointed as the ray-florets of 'DARK CHARM' (p.p. 7585). The vigor of the plant. The plant of 'CARTER' is more compact than 'DARK CHARM' (p.p. 7585).

The following is a description of the plant and characteristics that distinguish 'CARTER' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of CULTIVAR 'CARTER'

Bud:

*Size.*—Medium;cross-section 1.1 cm, height 1.0 cm.
*Outside color.*—Purple 75 A.
*Involucral bracts.*—2 rows, length 7 mm, width 3 mm.
*Involucral bracts among disc-florets.*—Not present.
*Involucral bracts color.*—Yellow-green 146 A.

Bloom:

*Type.*—Decorative.
*Height.*—Medium.
*Size.*—Large.
*Fully expanded.*—7.0–7.5 cm.
*Number of blooms per branch.*—Approx. 4 blooms per branch.
*Performance on the plant.*—5 weeks.
*Seeds.*—Not produced.
*Fragrance.*—Typical chrysanthemum.

Color:

*Color of upper surface of the ray-florets.*—Red-purple 74 C.
*Color of the lower surface of the majority of the ray-florets.*—Purple 75 A.
*Tonality from distance.*—A pot mum with large double pink flowers.
*Discoloration to color.*—To purple 75 A.

Ray florets:

*Texture.*—Upper and under side smooth.
*Number.*—80–85 (outer 4 rows excluding the tight center).
*Cross-section.*—Flat.
*Longitudinal axis of majority.*—Reflexing.
*Length of corolla tube.*—Medium.
*Ray-floret margin.*—Entire.
*Ray-floret length.*—3.5–3.8 cm.
*Ray-floret width.*—0.6–0.9 cm.
*Ratio length/width.*—High.
*Shape of tip.*—Round.
*Fragrance.*—Typical chrysanthemum.
*Disc florets.*—None.
*Receptacle shape.*—Domed raised.

Reproductive organs:

*Stamen* (*present in disc florets only*).—Not present.
*Pollen.*—Not present.
*Pollen color.*—Not applicable.
*Styles.*—Thin.
*Style color.*—Green 143 C.
*Style length.*—5 mm.
*Stigmas.*—Green 143 C.
*Stigma width.*—1 mm.
*Ovaries.*—Enclosed in calyx.

Plant:

*Type.*—A pot mum meant for indoor use.
*Growth habit.*—Spreading.
*Growth rate.*—Moderate.
*Height.*—24–26 cm.
*Width.*—25–27 cm.
*Quantity* (*number per lateral branch*).—5–7.
*Shape.*—Ovate.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Diverging.
*Shape of base.*—Asymmetric.
*Apex.*—Cuspidate.

Differences with the comparison varieties

| | 'CARTER' | 'DARK CHARM' |
|---|---|---|
| Ray-floret shape of tip | Round | Pointed |
| Vigor | Moderate | More vigorous |

I claim:

1. A new and distinct variety of chrysanthemum plant as described and illustrated.

* * * * *